US00PP18471P2

(12) United States Plant Patent
Hurkman

(10) Patent No.: US PP18,471 P2
(45) Date of Patent: Feb. 5, 2008

(54) ***PETUNIA* PLANT NAMED 'BALSUNWHITE'**

(50) Latin Name: *Petunia×hybrida*
Varietal Denomination: Balasunwhite

(75) Inventor: Margaret M. Hurkman, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/594,629

(22) Filed: Nov. 8, 2006

(51) Int. Cl.
*A01H 5/00* (2006.01)

(52) U.S. Cl. ..... Plt./356

(58) Field of Classification Search ..... Plt./356
See application file for complete search history.

(56) References Cited

PUBLICATIONS

UPOV ROM GTITM Computer Database, GIT JOUVE Retrieval Software Feb. 2007 Citation for 'Balsunwhite'.*

* cited by examiner

*Primary Examiner*—Wendy Haas
(74) *Attorney, Agent, or Firm*—Audrey Charles

(57) ABSTRACT

A new and distinct cultivar of *Petunia* plant named 'Balsunwhite', characterized by its single type white-colored flowers, medium green-colored foliage, and moderately vigorous, mounded-trailing growth habit.

1 Drawing Sheet

Latin name of genus and species of plant claimed: *Petunia×hybrida.*
Variety denomination: 'Balsunwhite'.

BACKGROUND OF THE INVENTION

The present invention relates to a new and distinct cultivar of *Petunia* plant botanically known as *Petunia×hybrida* and hereinafter referred to by the cultivar name 'Balsunwhite'.

The new cultivar originated in a controlled breeding program in Arroyo Grande, Calif. during November 2003. The objective of the breeding program was the development of *Petunia* cultivars with single type flowers, unique flower coloration, and a vigorous, mounded-trailing growth habit.

The new *Petunia* cultivar is the result of cross-pollination. The female (seed) parent of the new cultivar is Easy Wave White, not patented, characterized by its single type white-colored flowers, medium green-colored foliage, and prostrate-trailing growth habit. The male (pollen) parent of the new cultivar is the proprietary *Petunia×hybrida* breeding selection designated 2111-1, not patented, characterized by its single type cream white-colored flowers, medium green-colored foliage, and semi-upright growth habit. The new cultivar was discovered and selected as a single flowering plant within the progeny of the above stated cross-pollination during September 2004 in a controlled environment at Arroyo Grande, Calif.

Asexual reproduction of the new cultivar by terminal stem cuttings since September 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsunwhite' as a new and distinct cultivar of *Petunia* plant:

1. Single type white-colored flowers;
2. Medium green-colored foliage; and
3. Moderately vigorous, mounded-trailing growth habit.

Plants of the new cultivar differ from plants of the female parent primarily in growth habit and from plants of the male parent primarily in flower color and growth habit.

Of the many commercially available *Petunia* cultivars known to the inventor, the most similar in comparison to the new cultivar is Suncatcher White Improved 'Balsunwitim', not patented. However, in side by side comparisons, plants of the new cultivar differ from plants of 'Balsunwitim' in the following characteristics:

1. Plants of the new cultivar have a purer white flower color than plants of 'Balsunwitim'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsunwhite'. The plants were grown in 4.5 inch pots for 7 weeks in a greenhouse at West Chicago, Ill.

DETAILED BOTANICAL DESCRIPTION

Figure 1:
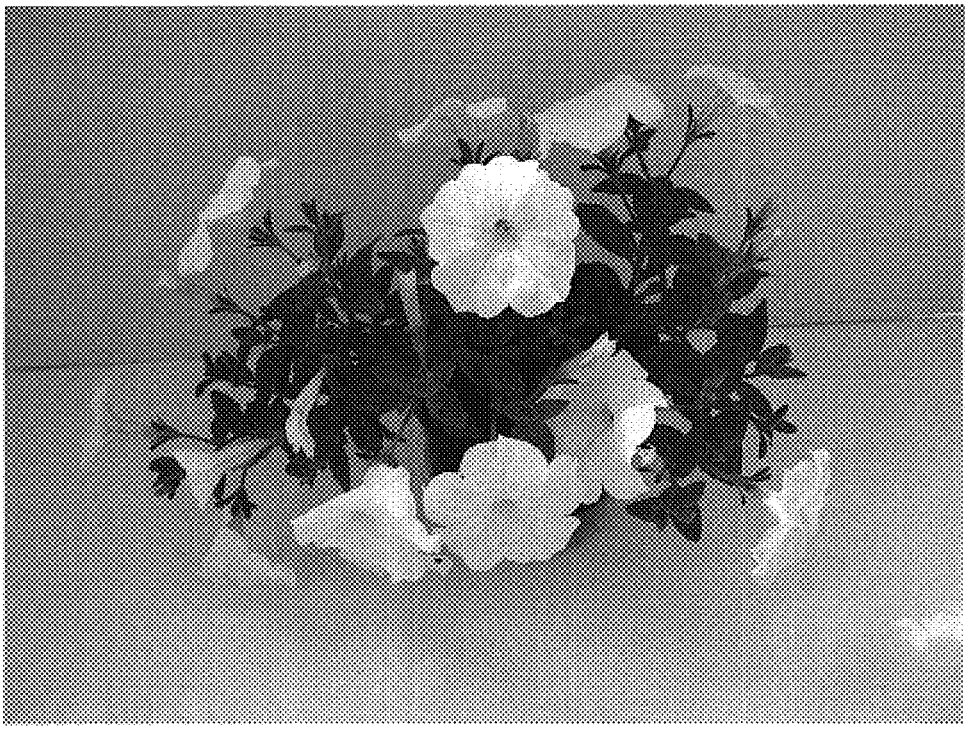
FIG. 1 illustrates a side view of the overall growth and flowering habit of 'Balsunwhite'.
Figure 2:
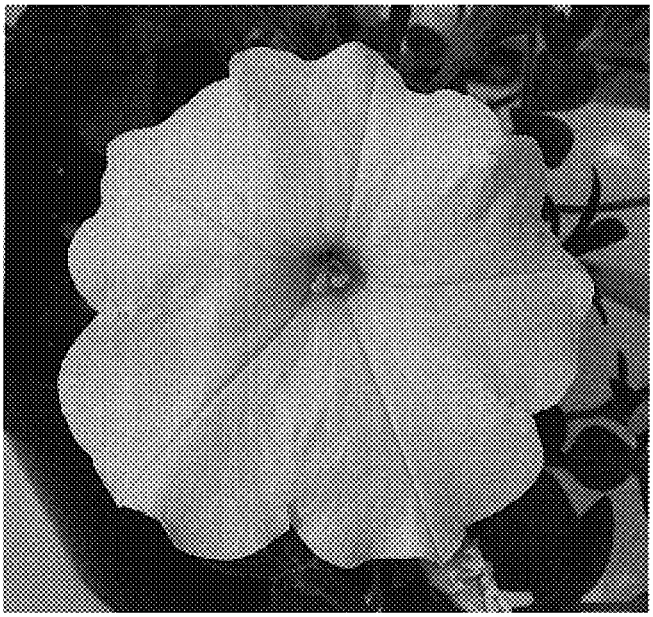
FIG. 2 illustrates a close-up view of an individual flower of 'Balsunwhite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary dictionary significance are used. The color values were determined on Aug. 15, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Petunia×hybrida* cultivar Balsunwhite.

Parentage:

*Female parent.*—Easy Wave White, not patented.

*Male parent.*—Proprietary *Petunia×hybrida* breeding selection designated 2111-1, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting.

*Growth habit and general appearance.*—Moderately vigorous, mounded-trailing.

*Size.*—Height from soil level to top of plant plane: Approximately 11.4 cm. Width: Approximately 25.4 cm.

*Branching habit.*—Freely branching. Quantity of main branches per plant: Approximately 3.

*Branch.*—Strength: Moderate. Length: Approximately 16.9 cm. Diameter: Approximately 2.7 mm. Length of central internode: Approximately 1.8 cm. Texture: Densely glandular pubescent with a mixture of long and short hairs. Gland color: Colorless. Color of young and mature stems: 144A.

Foliage description:

*General description.*—Quantity of leaves per main branch: Approximately 15. Fragrance: Slight. Form: Simple. Arrangement on flowering stem: Opposite.

*Leaves.*—Aspect: Acute angle to stem. Shape: Ovate. Margin: Entire. Apex: Acute. Base: Attenuate. Venation pattern: Pinnate. Length of mature leaf: Approximately 3.4 cm. Width of mature leaf: Approximately 2.0 cm. Texture of upper and lower surfaces: Densely glandular pubescent with a mixture of long and short hairs. Gland color: Colorless. Color of upper surface of young and mature foliage: 137B with venation of 143C. Color of lower surface of young and mature foliage: More yellow than 138A with venation of 143C.

*Petiole.*—Length: Approximately 3.2 mm. Width: Approximately 2.9 mm. Texture: Densely pubescent. Color: 143C.

Flowering description:

*Flowering habit.*—'Balsunwhite' is freely flowering under outdoor growing conditions with substantially continuous blooming from spring through autumn and year-round in greenhouse environment.

*Lastingness of individual flower on the plant.*—Approximately 9 to 11 days.

Flower description:

*General description.*—Type: Simple, salverform. Quantity per plant: Approximately 8. Fragrance: None.

*Bud.*—Rate of opening: Generally takes 1 to 2 days for bud to progress from first color to fully open flower. Quantity per plant: Approximately 3.

*Bud just before opening.*—Shape: Oblong. Length: Approximately 4.0 cm. Diameter at apex: Approximately 1.1 cm. Diameter at base: Approximately 3.8 mm. Texture: Densely glandular pubescent. Gland color: Colorless. Color of petals: 155D. Color of tube: 145D with venation of 145B.

*Corolla.*—Diameter: Approximately 6.2 cm.

*Petals.*—Quantity: 5, fused to form a tube. Shape: Obovate. Appearance: Velvety. Margin: Entire, wavy. Apex: Acute. Length from tube: Approximately 2.8 cm. Length of free portion: Approximately 1.5 cm. Width: Approximately 3.0 cm. Texture of upper surface: Glabrous. Texture of lower surface: Sparsely pubescent. Color of upper surface when first and fully open: Purer white than 155D with midveins of 145C. Color of lower surface when first and fully open: Purer white than 155D with midveins of 145B.

*Corolla tube.*—Length: Approximately 2.7 cm. Diameter at distal end: Approximately 1.3 cm. Diameter at proximal end: Approximately 3.0 mm. Texture of inner surface: Glabrous. Texture of outer surface: Densely pubescent. Color of inner surface: Purer white than 155D with venation of 145C. Color of outer surface: Purer white than 155D with an overlay of 145C and venation of 145B.

*Peduncle.*—Strength: Strong. Aspect: Acute angle to stem. Length: Approximately 3.4 cm. Diameter: Approximately 2.0 mm. Texture: Densely glandular pubescent with a mixture of long and short hairs. Gland color: Colorless. Color: 144A.

*Sepals.*—Quantity per flower: 5, fused along lower half. Shape: Linear. Apex: Acute. Length: Approximately 1.5 cm. Width: Approximately 3.0 mm. Texture of upper and lower surfaces: Densely glandular pubescent with a mixture of long and short hairs. Gland color: Colorless. Color of upper surface: 137A. Color of lower surface: 137B.

*Reproductive organs.*—Androecium: Stamen quantity: 5 per flower, partially fused to inside of corolla tube. Stamen length: Approximately 2 cm. Filament length of free portion: Approximately 1.4 cm. Filament color: Purer white than 155D. Anther shape: Bilobed. Anther length: Approximately 1.0 mm. Anther color: 158C. Pollen amount: Abundant. Pollen color: 155D. Gynoecium: Pistil quantity: 1 per flower. Pistil length: Approximately 2.4 cm. Stigma shape: Funnel. Stigma length: Approximately 1.0 mm. Stigma color: 143A. Style length: Approximately 2.0 cm. Style color: 145C. Ovary diameter: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balsunwhite', substantially as herein shown and described.

* * * * *